US012758790B2

(12) United States Patent
Fish et al.

(10) Patent No.: US 12,758,790 B2
(45) Date of Patent: Oct. 13, 2026

(54) BLANKET APPARATUS WITH MULTIPLE ELECTROMAGNETIC RADIATION SOURCES

(71) Applicants: Tyler Jordan Fish, San Diego, CA (US); Adam David Fischer, San Diego, CA (US)

(72) Inventors: Tyler Jordan Fish, San Diego, CA (US); Adam David Fischer, San Diego, CA (US)

(*) Notice: Subject to any disclaimer, the term of this patent is extended or adjusted under 35 U.S.C. 154(b) by 212 days.

(21) Appl. No.: 18/765,243

(22) Filed: Jul. 6, 2024

(65) Prior Publication Data

US 2025/0010099 A1 Jan. 9, 2025

Related U.S. Application Data

(60) Provisional application No. 63/512,254, filed on Jul. 6, 2023.

(51) Int. Cl.
*A61N 5/06* (2006.01)

(52) U.S. Cl.
CPC .... *A61N 5/0625* (2013.01); *A61N 2005/0636* (2013.01); *A61N 2005/0645* (2013.01); *A61N 2005/0652* (2013.01); *A61N 2005/0659* (2013.01); *A61N 2005/066* (2013.01); *A61N 2005/0663* (2013.01)

(58) Field of Classification Search
CPC .... A61N 2005/0636; A61N 2005/0645; A61N 2005/0663; A61N 2005/0659; A61N 5/0625; A61N 2005/0652
See application file for complete search history.

(56) References Cited

U.S. PATENT DOCUMENTS

| | | | | |
|---|---|---|---|---|
| 6,290,713 B1 * | 9/2001 | Russell | ................ | A61N 5/0616 607/91 |
| 2018/0228681 A1 * | 8/2018 | Iverson | .................... | A61H 1/00 |

FOREIGN PATENT DOCUMENTS

| | | | | |
|---|---|---|---|---|
| DE | 202018104580 U1 * | 8/2018 | ............... | A61F 7/08 |
| KR | 100702608 B1 * | 4/2007 | ........... | A47C 19/021 |

OTHER PUBLICATIONS

English Translation for DE 202018104580 (Year: 2018).*
English Translation for KR-100702608 (Year: 2018).*

* cited by examiner

*Primary Examiner* — Sean W Collins
(74) *Attorney, Agent, or Firm* — Sam Pierce

(57) ABSTRACT

A electromagnetic radiation apparatus comprising multiple electromagnetic radiation sources within a blanket, full body wrap or other covering, including a sleeping-bag-like device configured to cover at least a portion of a body. The sources may operate independently, separated or overlapped in time, simultaneously and/or in other coordinated fashion. A controller with at least two independent outputs is coupled to the first and second radiation sources for controlling emission parameters. The multiple sources may have different spectral content, e.g. envelope shape and nominal wavelength, and emission power. Electromagnetic shielding minimizes EMF exposure to the body.

20 Claims, 2 Drawing Sheets

BLANKET APPARATUS WITH MULTIPLE ELECTROMAGNETIC RADIATION SOURCES

BACKGROUND

The present invention relates to the field of devices that utilize electromagnetic radiation of specific wavelengths often used in the field of health and wellness. More specifically, the invention pertains to blankets, body wraps, sleeping bag-like devices or other coverings incorporating multiple sources of electromagnetic radiation whereby each source radiates at wavelengths different from the other source or sources.

Electromagnetic radiation has been used for various personal applications and has been studied for health benefits that may be provided. Two specific types of electromagnetic therapies that have gained popularity are red light therapy and far-infrared therapy. Far-infrared radiation provides a heating effect that is thought to penetrate deeper into tissues compared to traditional convective saunas. Benefits attributed to far-infrared therapy include deep muscle relaxation, detoxification, reduced inflammation, improved sleep, and stress relief. Similarly, near-infrared and middle-infrared, as described below, are also emerging and their benefits are widely considered valuable. Other emerging types gaining popularity are blue light therapy and near-infrared therapy. The electromagnetic radiation sources considered in this invention are all inclusive of wavelength whether the emission is in the visible or invisible electromagnetic spectrum. Therapy devices for animals other than humans may also use this apparatus. Therefore, the body inside the blanket may be other than human, such as a dog, horse, or other animal obtaining therapy in this way. Similarly, using this apparatus for plants may be found useful. In this specification, the word “body” will, by the inventor’s lexicography, refer to a human or other animal or plant body.

Red light therapy typically uses light sources such as light emitting diodes (LEDs) that emit radiation in the red portion of the visible spectrum, but can be more broadly chromatic as well. For example, light filtered to the red spectrum or narrow spectrum devices such as red lasers may be used. Exposure to red light has been associated with skin health improvements and potential cognitive and mental health benefits (US20030130709A1). Red light therapy is traditionally produced by panels of red lights with wavelengths generally in the range of 620-750 nm for total body exposure at several feet of distance from the body, or as face masks with built-in lighting sources that are strapped in close proximity to the face. Similarly, blue light therapy with a wavelength between 450-495 nm is emerging and used in a similar way.

Far-infrared therapy utilizes radiation in the far-infrared portion of the electromagnetic spectrum, typically defined as wavelengths between 3-1000 μm. Infrared saunas, similar in size and construction to conventional saunas but heated with far-infrared sources, are commonly used to deliver this therapy. Infrared saunas have the advantage of greater heat penetration of the tissues at a lower temperature, allowing the user to stay in longer.

In addition to red light and far-infrared sources, this invention discloses any sources of any wavelengths when multiple sources are included in the blanket device.

Different academic reference sources establish the cut off between named spectra at different wavelengths, herein, the inventor’s lexicography will be that the wording “red light source” is considered to include an emitter that falls somewhere in at least the range 0.62-0.75 μm in wavelength but may be outside of that range, “near-infrared” is considered to include an emitter that falls somewhere in at least the range 0.75-1.1 μm but may be outside that range, middle infrared to include at least the range 1.1-3 μm but may be outside that range, and “far-infrared” to include an emitter that falls somewhere in at least the range 3-1000 μm but may be outside that range. These numbers are not intended to limit the invention but to explain and make clear the disclosure. The claims will apply to multiple sources of different spectral content regardless of their specific name or wavelength.

When multiple sources are used simultaneously a compound effect on the body may be obtained that is greater than the individual effects. Also, when operated simultaneously, they may provide exposure to each in overlapping time periods so as to reduce the total time needed for exposure to each source individually using individual serialized exposures.

The infrared blanket device is commercially available in order to provide the two-fold benefit of a small form factor compared to a sauna, and also to operate low power infrared exposure in close proximity to the body. Similarly, a red-light therapy full body blanket device exists commercially.

However, there are no blankets or full or near-full body coverings in the prior art that provide the combination of infrared and red-light, or any other multi-spectral proximity exposure. The prior art does not disclose a device that combines both of these therapies into a single apparatus.

Therefore, there remains a need for devices that can provide the benefits of multiple electromagnetic therapies, including both red light therapy and infrared therapy, simultaneously in a compact, format. Specifically, there is a need for a device that can irradiate large areas of the body with both multiple electromagnetic sources, such as red-light and infrared radiation in close proximity to the body. The present invention fulfills this need by incorporating multiple electromagnetic radiation sources within a blanket, body wrap or other covering, with independent controls for each source on the amount and technique for exposure.

Delivering the above referenced electromagnetic energy to the body is currently used as a popular form of therapy in the health industry, however, there are no specific biological transformations or specific health benefits that the apparatus claimed in this invention depends upon. The herein claimed apparatus provides the desired therapy in a preferred way, and the word “therapy” is used in the inventor’s lexicography in this specification to describe the accepted process of irradiating a body to the electromagnetic radiation but not the actual therapeutic nature of the therapy for any specific ailment as that is a medical process beyond the scope of this invention.

SUMMARY

The present invention is an electromagnetic radiation apparatus that provides multiple electromagnetic radiation sources in a blanket or full body wrap device. In an exemplary embodiment, the apparatus includes a blanket or covering configured to wrap around or cover at least a portion of a body in close proximity. In the exemplary embodiment, inside the blanket are a first electromagnetic radiation source that emits in the red light spectrum between 620-750 nm, such as an array of red LEDs, which may cover the entirety of the inside of the blanket with red light at a what is considered a therapeutic level, and a second electromagnetic radiation source that emits in the far-infrared spectrum between 3-1000 μm, such as carbon-fiber wires that meander throughout the entire blanket, heat up, and emit black-body radiation, when current is passed through them.

A controller with at least two independent outputs is coupled to the one or more radiation sources. This allows the controller to independently control parameters such as the intensity, duty cycle, and waveform of each source. The apparatus may optionally include additional radiation sources at different wavelengths, such as blue light between 450-495 nm.

The radiation sources are arranged throughout the interior of the blanket to irradiate large areas of the body at once. Electromagnetic shielding, such as grounded wires can be wrapped around the power leads in a helical pattern, is used to minimize EMF exposure to the body. The blanket may be made of a waterproof polyurethane material that traps heat to enhance the effect. In the inventor's lexicography, an electromagnetic source may be a group of emitters with a common characteristic, such as an array of many red-light emitting LEDs. Though each LED may also be considered a source, the common characteristic is referred to a electromagnetic source. Similarly, the array may be broken up into multiple sub-arrays such that different parts of the body may receive exposure that is controlled differently (e.g. power level, time waveform, etc.). The user may use the controller for that electromagnetic source to set the exposure type and value for each sub-array or sub-area of the body.

In an exemplary embodiment, the blanket is wrapped around or laid over the body. The controller is used to activate the red and infrared radiation sources. This provides an enhanced synergistic effect compared to either therapy alone. The portability of the blanket apparatus allows it to be used in a variety of locations and in closer proximity to the body compared to a traditional sauna. Proximity enables a higher intensity exposure with lower energy requirements than a traditional sauna with light therapy.

Additional features and advantages of the invention will be set forth in the description which follows, and in part will be obvious from the description, or may be learned by the practice of the invention. These and other features of the present invention will become more fully apparent from the following description, or may be learned by the practice of the invention as set forth hereinafter.

BRIEF DESCRIPTION OF THE DRAWINGS

The various exemplary embodiments of the present invention, which will become more apparent as the description proceeds, are described in the following detailed description in conjunction with the accompanying drawings, in which.

DETAILED DESCRIPTION

Figure 1:
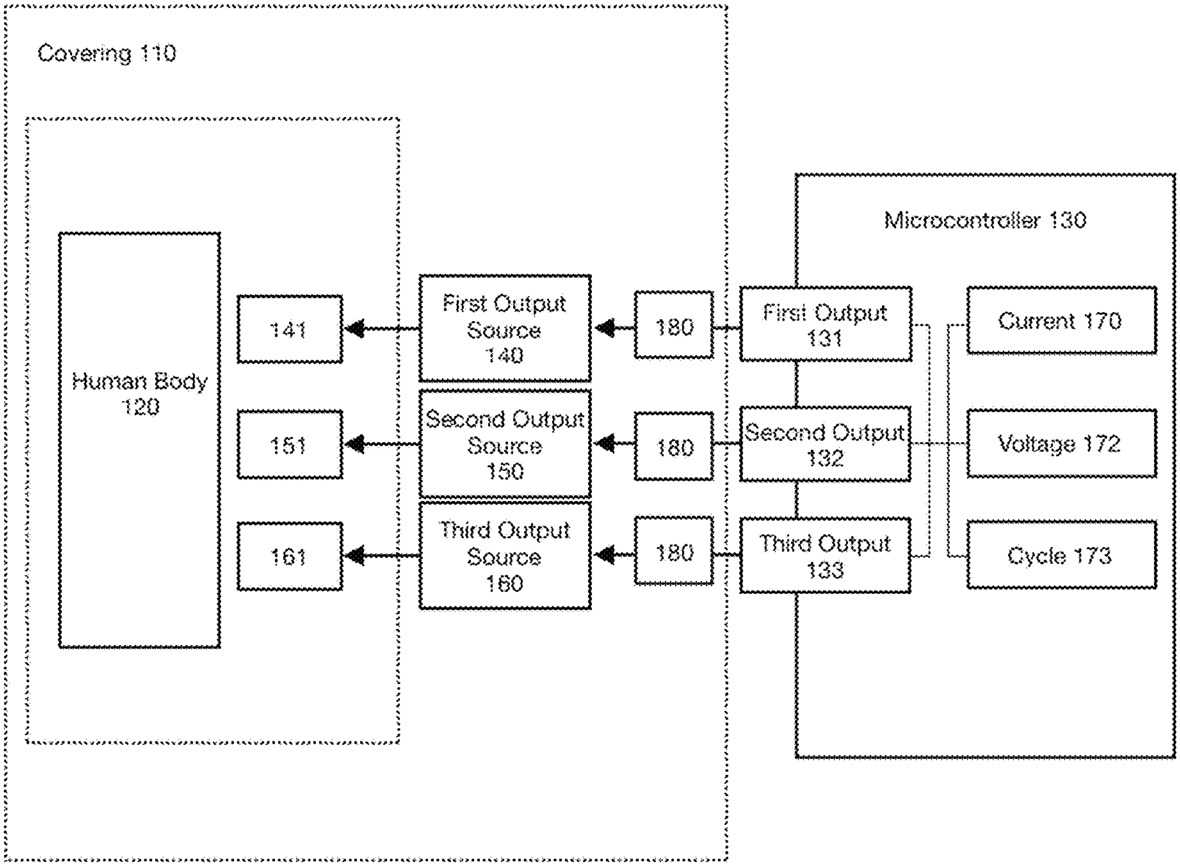
FIG. 1 is an apparatus diagram illustrating an embodiment of the electromagnetic radiation apparatus.

In the following detailed description of the preferred embodiments, reference is made to the accompanying drawings, which form a part hereof and show, by way of illustration, specific embodiments in which the invention may be practiced. It is to be understood that other embodiments may be used and structural or logical changes may be made without departing from the scope of the present invention. The following detailed description, therefore, is not to be taken in a limiting sense, and the scope of the present invention is defined by the appended claims.

The following description is provided as an enabling teaching of the present apparatuses, and/or methods in its best, currently known aspect. To this end, those skilled in the relevant art will recognize and appreciate that many changes can be made to the various aspects of the present apparatuses described herein, while still obtaining the beneficial results of the present disclosure. It will also be apparent that some of the desired benefits of the present disclosure can be obtained by selecting some of the features of the present disclosure without utilizing other features.

Accordingly, those who work in the art will recognize that many modifications and adaptations to the present disclosure are possible and can even be desirable in certain circumstances and are a part of the present disclosure. Thus, the following description is provided as illustrative of the principles of the present disclosure and not in limitation thereof.

The terms "a" and "an" and "the" and similar references used in the context of describing a particular embodiment of the present invention (especially in the context of certain claims) are construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein.

All apparatuses described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application. Thus, for example, reference to "an element" can include two or more such elements unless the context indicates otherwise.

As used herein, the terms "optional" or "optionally" mean that the subsequently described event or circumstance can or cannot occur, and that the description includes instances where said event or circumstance occurs and instances where it does not.

The word or as used herein means any one member of a particular list and also includes any combination of members of that list. Further, one should note that conditional language, such as, among others, "can," "could," "might", or "may" unless specifically stated otherwise, or otherwise understood within the context as used, is generally intended to convey that certain aspects include, while other aspects do not include, certain features, elements and/or steps. Thus, such conditional language is not generally intended to imply that features, elements and/or steps are in any way required for one or more particular aspects or that one or more particular aspects necessarily include logic for deciding, with or without user input or prompting, whether these features, elements and/or steps are included or are to be performed in any particular aspect.

In one exemplary embodiment, the electromagnetic radiation apparatus includes both carbon-fiber wires configured to generate far-infrared electromagnetic radiation and an array of red light emitting diodes (LEDs) configured to generate red light therapy. The carbon-fiber wires and red LEDs are both disposed within the interior of the blanket in an interspersed arrangement to allow simultaneous irradiation of the body with both far-infrared and red light when the blanket is in use. In other exemplary embodiments, other or additional electromagnetic sources emitting in different parts of the spectrum, such as blue light between 450-495 nm or green light between 495-570 nm, may be combined together with the red and infrared sources in a multiple wavelength therapy blanket. The blanket is not required to include both near-infrared and far-infrared sources in every embodiment, and some implementations may only utilize one of the infrared wavelength ranges.

In the exemplary embodiment, the combination of both red light therapy and far-infrared therapy are included in the same treatment blanket. The red light, having a relatively shorter wavelength between 620-750 nm, penetrates into the skin and outer muscle tissue in an effort to provide healing, rejuvenating and anti-inflammatory effects. Red and near-infrared light therapy has also been clinically studied to provide cognitive and psychological benefits such as improved mood and sleep. The far-infrared radiation, with a longer wavelength between 3-1000 μm, is thought to penetrate deeper to warm the muscles, bones, and joints. Far-infrared therapy often targets detoxification, muscle relaxation, reduction of inflammation, decreased stress, and improved sleep quality.

Each wavelength range targets different tissue depths and produces different biological responses. The combination may amplify the benefits of each allowing the body to better relax and heal through the variety of wavelengths. For example, with the outer muscle more relaxed from the red light therapy, the inner muscle may more easily relax and get increased benefits from the far infrared. With the inner muscle more relaxed, the outer muscle and skin may be more relaxed, allowing for increased benefits from the red light.

The close conformal proximity of the red and infrared sources to the body when disposed within the therapy blanket allows for a higher intensity of wavelengths to be applied using a lower input power compared to a conventional sauna enclosure where the sources are farther away.

FIG. 1 is an apparatus diagram illustrating an exemplary embodiment of an electromagnetic radiation apparatus (100). The apparatus (100) includes a blanket, full body wrap, or covering (110) configured to wrap around or cover at least a portion of a human body (120) in close proximity.

The apparatus (100) further includes a microcontroller-based controller (130) having at least a first output (131), a second output (132), and optionally a third output (133) and optionally more outputs not shown in the figures. The controller (130) utilizes a modulation which may be independently selected to drive the outputs (for example, stead state DC, pulse width modulation, sinusoidal or generalized wave shaping modulation). This microcontroller provides sufficient processing power while minimizing power consumption. A first electromagnetic radiation source (140) is coupled to the first output (131) of the controller (130). The first electromagnetic radiation source (140) comprises a plurality of emitting sources configured to emit near-infrared radiation in a first wavelength range (141) of 800-950 nm. In some embodiments the emitting sources are high-power infrared emitters. The first electromagnetic radiation source (140) is positioned inside the blanket, full body wrap, or covering (110) between the blanket, full body wrap, or covering (110) and the body (120).

A second electromagnetic radiation source (150) is coupled to the second output (132) of the controller (130). The second electromagnetic radiation source (150) comprises a plurality of light emitting diodes configured to emit red light in a second wavelength range (151) of 600-700 nm, different from the first wavelength range (141). The second electromagnetic radiation source (150) is also positioned inside the blanket, full body wrap, or covering (110) between the blanket, full body wrap, or covering (110) and the body (120).

In some embodiments, the apparatus (100) may further include a third electromagnetic radiation source (160) coupled to the third output (133) of the controller (130). The third electromagnetic radiation source (160) comprises a plurality of light emitting sources configured to emit blue light in a third wavelength range (161) of 400-495 nm, different from the first wavelength range (141) and the second wavelength range (151). The third electromagnetic radiation source (160) is also positioned inside the blanket, full body wrap, or covering (110) between the blanket, full body wrap, or covering (110) and the body (120). In some embodiments the apparatus may include further electromagnetic radiation sources configured in similar or different configurations than the initial three mentioned herein.

The controller (130) is configured to independently control the first electromagnetic radiation source (140) and the second electromagnetic radiation source (150) via the first output (131) and the second output (132), respectively, to provide electromagnetic radiation to the body (120). The controller (130) may independently control various parameters of each radiation source, comprising current (170) using a constant current driver, voltage (171) using a voltage regulator, duty cycle (172) using PWM, and/or waveform shape (173) using an arbitrary waveform generator.

In some embodiments, the apparatus (100) may further include electromagnetic shielding (180) around the wires (181) that provide current to the first electromagnetic radiation source (140) and the second electromagnetic radiation source (150). The electromagnetic shielding (180) helps reduce electromagnetic field (EMF) radiation (182) exposure to the body (120). The electromagnetic shielding (180) may include grounded copper braided sleeving or aluminum foil wrapped around the wires (181) that provide current to the radiation sources in a helical configuration.

The apparatus (100) enables a method of providing electromagnetic radiation. The method includes coupling the first electromagnetic radiation source (140) to the first output (131) of the controller (130), coupling the second electromagnetic radiation source (150) to the second output (132) of the controller (130), and independently controlling the first electromagnetic radiation source (140) and the second electromagnetic radiation source (150) via the controller (130) to emit electromagnetic radiation directed toward the human body (120). The method may further include coupling the third electromagnetic radiation source (160) to the third output (133) of the controller (130) and independently controlling the third electromagnetic radiation source (160) via the controller (130). The radiation sources may be controlled using a closed-loop feedback system that monitors the output power, wavelength, and/or temperature of the LEDs and adjusts the driving parameters accordingly. The feedback system may include photodiodes, thermistors, or other sensors that provide real-time measurement data to the controller.

The apparatus may also include shielding of the first electromagnetic radiation source (140) and the second electromagnetic radiation source (150) using the electromagnetic shielding (180) to protect the human body (120) from low frequency or extremely low frequency electromotive force (LF-EMF or ELF-EMF) radiation emitted by the wires carrying current to the radiation sources. The shielding may be grounded to a common point such as the negative terminal of the power supply or the chassis of the controller to prevent ground loops and reduce interference. Independently controlling the radiation sources may involve varying at least one of current (170) using a digital potentiometer, voltage (172) using a digital-to-analog converter, duty cycle (173) using a microcontroller's PWM functionality, or amplitude of a driving waveform using a digital signal processor supplied by the controller (130) to each radiation source.

Figure 2:
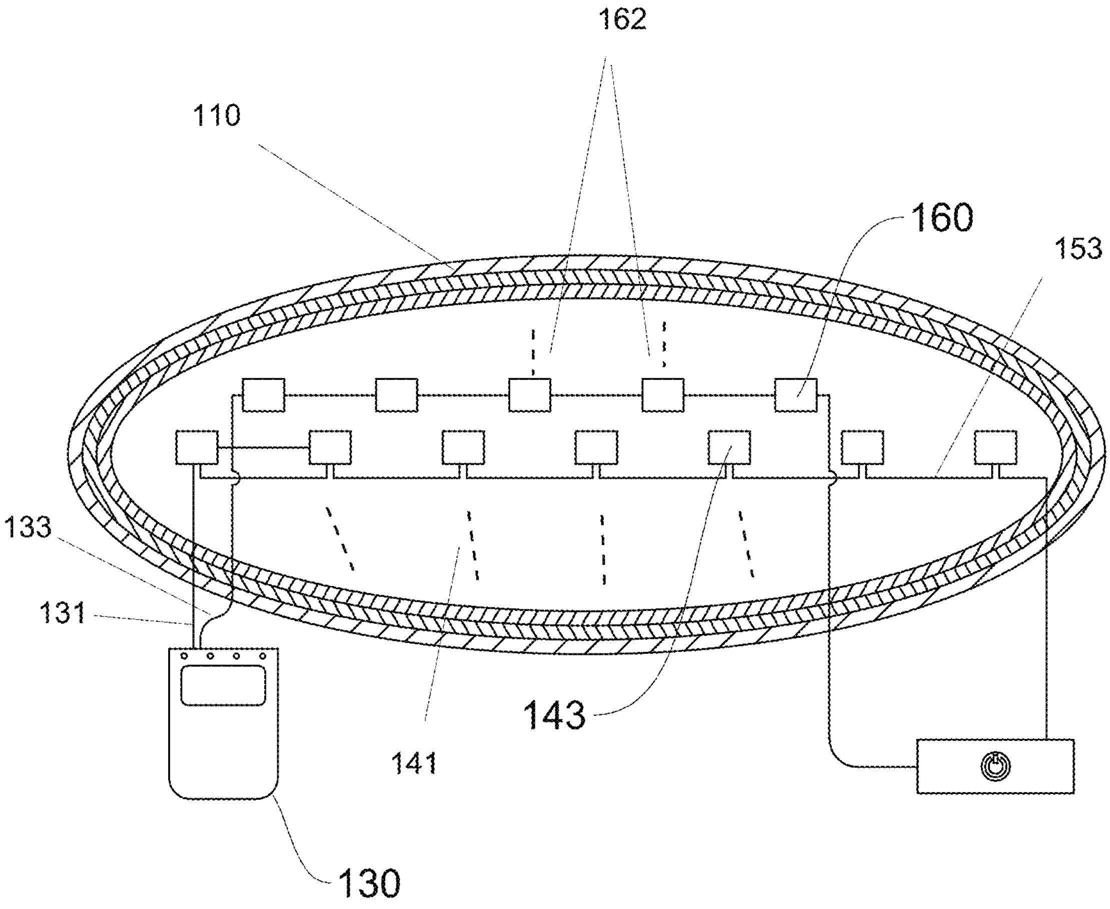
FIG. 2 shows a cross-sectional view of the blanket, full body wrap, or covering of the electromagnetic radiation apparatus.

FIG. 2 shows a cross-sectional view of the blanket, full body wrap, or covering (110) of the electromagnetic radiation apparatus. The blanket (110) comprises multiple layers of material with various electromagnetic radiation sources embedded within.

A plurality of red-light emitting sources (143) are distributed throughout the blanket (110). The red-light emitting sources (143) are configured to emit electromagnetic radiation in a first wavelength range (141) in the red light spectrum between 620 nm and 750 nm when powered by a first output (131) from the controller (130).

A series of wires (153) meander throughout the layers of the blanket (110). The wires (153) act as a second electromagnetic radiation source configured to emit radiation in a second wavelength range in the far-infrared spectrum between 3 μm and 1000 μm when electrical current from a second output (133) of the controller is passed through the wires (153).

Optionally, the blanket (110) may also include one or more blue light emitting sources as a third electromagnetic radiation source (160) coupled to a third output of the controller. The blue LEDs (160) emit radiation (162) in a third wavelength range in the blue light spectrum between 450 nm and 495 nm.

To reduce electromagnetic field (EMF) radiation exposure to the human body, the wires that provide current to the various radiation sources are wrapped with electromagnetic shielding. The electromagnetic shielding may comprise grounded wires wrapped around the current-carrying wires in a helical configuration.

The controller can independently control the various radiation sources by varying parameters such as the current, voltage, duty cycle, and waveform shape provided at its outputs. This allows the intensity and duration of radiation exposure to be precisely controlled for each wavelength range to provide effects.

The embodiments described herein are given for the purpose of facilitating the understanding of the present invention and are not intended to limit the interpretation of the present invention. The respective elements and their arrangements, materials, conditions, shapes, sizes, or the like of the embodiment are not limited to the illustrated examples but may be appropriately changed. Further, the constituents described in the embodiment may be partially replaced or combined together.

What is claimed is:

1. An electromagnetic radiation apparatus, comprising:

a blanket, full body wrap, or covering configured to wrap around or cover at least a portion of a body;

a controller having at least two independent outputs;

a first electromagnetic radiation source coupled to a first output of the controller, the first electromagnetic radiation source configured to emit radiation in a first wavelength range, wherein the first electromagnetic radiation source comprises a plurality of light emitting sources distributed throughout the blanket, full body wrap, or covering and configured to be positioned inside the blanket, full body wrap, or covering between the blanket, full body wrap, or covering and the body; and a second electromagnetic radiation source coupled to a second output of the controller, the second electromagnetic radiation source comprising one or more wires configured to meander throughout the blanket, full body wrap, or covering and configured to emit far-infrared radiation as black-body radiation in a second wavelength range in a far-infrared spectrum between 3 micrometers and 1000 micrometers when electrical current is passed through the one or more wires, wherein the second electromagnetic radiation source is configured to be positioned inside the blanket. full body wrap, or covering between the blanket, full body wrap, or covering and the body;

wherein the controller is configured to independently control drive parameters of each of the first electromagnetic radiation source and the second electromagnetic radiation source.

2. The electromagnetic radiation apparatus of claim 1, wherein the first wavelength range is in a red light spectrum between 620 nm and 750 nm.

3. The electromagnetic radiation apparatus of claim 1, wherein the first wavelength range is in a blue light spectrum between 450 nm and 495 nm.

4. The electromagnetic radiation apparatus of claim 1, wherein the blanket, full body wrap, or covering is configured as a sleeping-bag-like enclosure that substantially encloses the body.

5. The electromagnetic radiation apparatus of claim 1, wherein the controller is configured to control a voltage supplied to one of the first electromagnetic radiation source and the second electromagnetic radiation source, and a current supplied to the other of the first electromagnetic radiation source and the second electromagnetic radiation source.

6. The electromagnetic radiation apparatus of claim 1, wherein the controller is configured to control a voltage supplied to one of the first electromagnetic radiation source and the second electromagnetic radiation source, and a duty cycle of a drive signal supplied to the other of the first electromagnetic radiation source and the second electromagnetic radiation source.

7. The electromagnetic radiation apparatus of claim 1, wherein the controller is configured to control a voltage supplied to one of the first electromagnetic radiation source and the second electromagnetic radiation source, and a waveform shape of a drive signal supplied to the other of the first electromagnetic radiation source and the second electromagnetic radiation source.

8. The electromagnetic radiation apparatus of claim 1, wherein the controller is configured to control a current supplied to one of the first electromagnetic radiation source and the second electromagnetic radiation source, and a duty cycle of a drive signal supplied to the other of the first electromagnetic radiation source and the second electromagnetic radiation source.

9. The electromagnetic radiation apparatus of claim 1, wherein the controller is configured to control a current supplied to one of the first electromagnetic radiation source and the second electromagnetic radiation source, and a waveform shape of a drive signal supplied to the other of the first electromagnetic radiation source and the second electromagnetic radiation source.

10. The electromagnetic radiation apparatus of claim 1, wherein the drive parameters independently controlled by the controller comprise, for at least one of the first electromagnetic radiation source and the second electromagnetic radiation source, a waveform shape of a drive signal, the waveform shape comprising a duty cycle of the drive signal and an amplitude of an on-time portion of the drive signal, the amplitude comprising at least one of a voltage amplitude and a current amplitude of the drive signal.

11. A method of providing electromagnetic radiation, the method comprising:

providing a blanket, full body wrap, or covering configured to wrap around or cover at least a portion of a body, the blanket, full body wrap, or covering comprising:

a first electromagnetic radiation source configured to emit radiation in a first wavelength range, wherein the first electromagnetic radiation source comprises a plurality of light emitting sources distributed throughout the blanket, full body wrap, or covering and configured to be positioned inside the blanket, full body wrap, or covering between the blanket, full body wrap, or covering and the body; and a second electromagnetic radiation source comprising one or more wires configured to meander throughout the blanket, full body wrap, or covering and configured to emit far-infrared radiation as black-body radiation in a second wavelength range in a far-infrared spectrum between 3 micrometers and 1000 micrometers when electrical current is passed through the one or more wires, the second electromagnetic radiation source configured to be positioned inside the blanket, full body wrap, or covering between the blanket, full body wrap, or covering and the body:

coupling the first electromagnetic radiation source to a first output of a controller;

coupling the second electromagnetic radiation source to a second output of the controller; and independently controlling, by the controller, drive parameters of each of the first electromagnetic radiation source and the second electromagnetic radiation source to emit electromagnetic radiation directed toward the body.

12. The method of claim 11, wherein the first wavelength range is in a red light spectrum between 620 nm and 750 nm.

13. The method of claim 11, wherein the first wavelength range is in a blue light spectrum between 450 nm and 495 nm.

14. The method of claim 11, wherein the blanket, full body wrap, or covering is configured as a sleeping-bag-like enclosure that substantially encloses the body.

15. The method of claim 11, wherein independently controlling drive parameters comprises controlling a voltage supplied to one of the first electromagnetic radiation source and the second electromagnetic radiation source, and a current supplied to the other of the first electromagnetic radiation source and the second electromagnetic radiation source.

16. The method of claim 11, wherein independently controlling drive parameters comprises controlling a voltage supplied to one of the first electromagnetic radiation source and the second electromagnetic radiation source, and a duty cycle of a drive signal supplied to the other of the first electromagnetic radiation source and the second electromagnetic radiation source.

17. The method of claim 11, wherein independently controlling drive parameters comprises controlling a voltage supplied to one of the first electromagnetic radiation source and the second electromagnetic radiation source, and a waveform shape of a drive signal supplied to the other of the first electromagnetic radiation source and the second electromagnetic radiation source.

18. The method of claim 11, wherein independently controlling drive parameters comprises controlling a current supplied to one of the first electromagnetic radiation source and the second electromagnetic radiation source, and a duty cycle of a drive signal supplied to the other of the first electromagnetic radiation source and the second electromagnetic radiation source.

19. The method of claim 11, wherein independently controlling drive parameters comprises controlling a current supplied to one of the first electromagnetic radiation source and the second electromagnetic radiation source, and a waveform shape of a drive signal supplied to the other of the first electromagnetic radiation source and the second electromagnetic radiation source.

20. The method of claim 11, wherein independently controlling drive parameters comprises, for at least one of the first electromagnetic radiation source and the second electromagnetic radiation source, controlling a waveform shape of a drive signal, the waveform shape comprising a duty cycle of the drive signal and an amplitude of an on-time portion of the drive signal, the amplitude comprising at least one of a voltage amplitude and a current amplitude of the drive signal.

* * * * *